United States Patent [19]

Farr et al.

[11] Patent Number: 4,741,915

[45] Date of Patent: May 3, 1988

[54] PROTECTION OF FOODSTUFFS FROM OXIDATION

[75] Inventors: David R. Farr, Brent; Danièle Magnolato, La Tour-de-Peilz; Jürg Löliger, Corseaux, all of Switzerland

[73] Assignee: Nestec S.A., Vevey, Switzerland

[21] Appl. No.: 624,953

[22] Filed: Jun. 27, 1984

[30] Foreign Application Priority Data

Jul. 6, 1983 [CH] Switzerland ............... 3707/83

[51] Int. Cl.$^4$ ............................................. A23L 1/42
[52] U.S. Cl. ................................... 426/542; 426/655; 536/4.1
[58] Field of Search ............. 426/541, 268, 270, 542, 426/545, 546, 629, 655, 425, 427, 428, 430; 536/4.1, 18.1

[56] References Cited

U.S. PATENT DOCUMENTS

| | | | |
|---|---|---|---|
| 2,354,719 | 1/1942 | Verbeck | 426/546 |
| 2,768,084 | 10/1956 | Griffith et al. | 99/163 |
| 2,772,169 | 11/1956 | Hall | 99/159 |
| 4,387,094 | 6/1983 | Bagros | 514/562 |
| 4,465,673 | 8/1984 | Tanaka et al. | 536/18.1 |

FOREIGN PATENT DOCUMENTS 103383 6/1983 Japan.

OTHER PUBLICATIONS

Weast 1970 Handbook of Chemistry and Physics. CRC Press Cleveland OH pp. C193, C311 and 503.
Winton et al 1935 The Structure and Composition of Foods J. Wiley & Sons NY pp. 671–676.
Tumble 1892 The Tannins J. Lippincott Co. Philadelphia pp. 78–87.
Grant 1969 Hackh's Chemical Dictionary McGraw-Hill Book Co. New York pp. 250, 290, 301, 303 and 660.

*Primary Examiner*—Raymond N. Jones
*Assistant Examiner*—Carolyn Paden
*Attorney, Agent, or Firm*—Vogt & O'Donnell

[57] ABSTRACT

Antioxidants containing purified and hydrolyzed gallotannins are derived from plant materials and are incorporated into foodstuffs for inhibiting oxidation in the foodstuffs.

9 Claims, No Drawings

PROTECTION OF FOODSTUFFS FROM OXIDATION

BACKGROUND OF THE INVENTION

The present invention relates to the protection of foodstuffs and cosmetic products against the effects of oxygen.

Anti-oxidants for use in foodstuffs or cosmetics should have good anti-oxidant activity, be stable, colourless, organoleptically neutral and should be guaranteed to be harmless.

Known anti-oxidants, which are widely used, are obtained synthetically and are generally phenolic materials, for example butylhydroxyanisole (B.H.A.) and butylhydroxytoluene (B.H.T.), individually or in synergistic mixtures. Other phenolic derivatives are known to have anti-oxidant properties, for example pyrogallol which suffers from the disadvantages of being relatively toxic, or gallates, more particularly propyl, octyl, or lauryl gallates. Although these materials unmistakeably have anti-oxidant activity, good stability, are colourless and are acknowledged as being harmless and neutral with respect to food, their use is in the process of being vigorously challenged by a number of food laws.

Attempts have been made to utilise the fact that certain natural products contain anti-oxidants. A good many fatty substances, for example, are protected naturally against oxidation by the tocopherols which they contain, but their activity is poor. Proposals have also been made to extract the anti-oxidants contained in plant matter, such as spices and more particularly in Labiatae, such as sage or rosemary. The proposed methods make use of a chemical agent and are therefore questionable for the same reason as synthetic antioxidants or necessitate the extraction by solvents of crushed plant matter, generally followed by elaborate treatments for distilling, decolourisation and deodorization of the extracts. Even if the anti-oxidant activity of these extracts is acknowledged their use is limited because in almost every case there remains some lingering colour, smell and taste of the spice which was used.

A proposal has been made in Japanese patent No. 71.039.058 to protect sea foods from oxidation by adding catechols, gallocatechols and 3-galloyl derivatives of these compounds which are condensed natural tannins and consist principally of esters of gallic acid and flavan-3-ols which are found in tea leaves. According to this patent the anti-oxidant compounds are extracted, i.e., by ethanol. The colour is removed from the extract by active carbon and the solvent is evaporated.

SUMMARY OF THE INVENTION

The present invention is based on the surprising fact that some natural hydrolysable tannins which have been extracted from widely-available plants have an anti-oxidant activity much greater than that of condensed tannins of tea, whilst being remarkably neutral from the point of view of colour, smell and taste.

The present invention thus relates to a method of protecting foodstuffs and cosmetic products against the effects of oxygen, characterised in that an effective amount of gallotannins extracted from plant matter are incorporated into the product to be protected. These gallotannins consist of polymers of gallic acid and an alicyclic polyol or a sugar in a molecular ratio or gallic acid/polyol or sugar of from 2 to 20 to 1.

DETAILED DESCRIPTION OF THE INVENTION

The proposed gallotannins are esters of gallic acid corresponding to the formula:

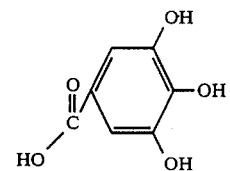

with an alicyclic polyol or a sugar, more particularly glucose. Unlike the high molecular weight condensed tannins, these are hydrolysable compounds which have a molecular weight of from 300 to 5,000 and more particularly from 900 to 2,000. In the polymer, which may be polygalloylglucose, the ratio of the molecules of gallic acid to the molecules of glucose is preferably from 2 to 11.

These gallotannins are hydrolysable, thereby indicating that they may be easily degraded into their constituent fragments of lower molecular weight by the action of enzymes, hot water, acids and bases. They consist of a base nucleus which is the alicyclic polyol or sugar, the alcohol functions of which are more or less esterified by gallic acid or by the complex forms of gallic acid involving depsidic bonds (bonds between two galloyl groups). Unlike the gallocatechols of tea, the polyol is not condensed or polycyclic but is generally glucose (hexose), occasionally hamamelose (pentose) or even quinic acid corresponding to the formula:

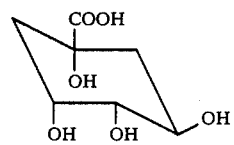

Gallotannins, which are widely found in the plant kingdom come from the roots, pods, fruit pulp, leaves or parasites of plants, such as the galls of the wood and bark of trees.

"Chinese tannin" or tannic acid from galls of *Rhus semialata*, "Sumach tannin" from the leaves of *Rhus typhina* and "Turkish gallotannin" from the galls of the wood and bark of *Quercus infectoria*, for example, correspond to the formula:

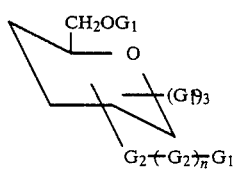

in which $G_1$ is a gallic acid residue corresponding to the formula:

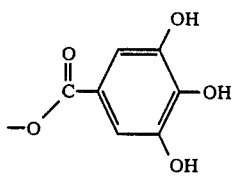

$G_2$ is a gallic acid residue corresponding to the formula:

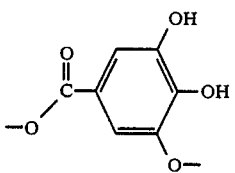

n is 0, 1 or 2 and the base nucleus is penta-galloyl glucose. The $G_2$-$[G_2]_n$-$G_1$ group may be in the 2, 3 or 4 position and the $G_1$ groups occupy the free positions.

"Tara tannin" from the fruits or pods of *Caesalpinia spinosa* corresponds to the formula:

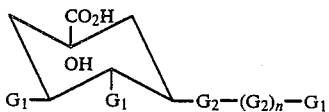

in which $G_1$ and $G_2$ are as defined above, n is 0, 1 or 2 and the base nucleus is trigalloyl-quinic acid.

Other examples include "Acer tannin" from the leaves of *Acer ginnale*, the sugar of which is 1,5-anhydro-glucitol and "Hamameli tannin" from the bark of *Hamamelis virginica*, the sugar of which is hamamelose or α-oxymethyl-ribose.

An advantageous source of gallotannins are the pods of green carob, *Ceratonia siliqua*, which is widely found and which may be used raw or in the form of a desugared residue from the extraction in water of carob flour.

DESCRIPTION OF THE PREFERRED EMBODIMENTS

According to the first embodiment, the plant matter is extracted by a water-miscible solvent, such as ethanol, methanol or acetone, ethyl alcohol being preferred as it is comestible. A mixture of ethyl alcohol and water, with an alcohol content of from 90 to 96%, is advantageously used. The weight proportion of solvent/plant matter is from 100/1 to 5/1 and is preferably 20/1. The ground plant matter is extracted at a temperature of from 20° C. to the boiling temperature of the solvent which is used for from 5 to 30 mins. The solvent is subsequently evaporated under vacuum at a temperature of from 20° to 50° C., depending on the solvent which is used and the vacuum which is applied. In this manner a crude extract is obtained which may be used immediately in the products to be protected.

According to the second embodiment, the dried crude extract is purified by taking it up in a mixture of water-immiscible organic solvent and water, ethyl acetate and water for example, in a proportion by volume of about 1/1, at an almost neutral pH for, example, from 6.8 to 7, and preferably at ambient temperature. About 20 parts of extraction liquid are used per 1 part by weight of crude extract. This enables the gallotannins to be separated from the water-soluble compounds and more particularly from the gallic acids. The organic phase is separated and the solvent is evaporated under reduced pressure at a temperature of from 20° to 50° C., depending on the solvent which is used and the vacuum which is applied. This purified extract contains essentially tannic acid and may be incorporated in this state into the products to be protected.

According to the third, preferred, embodiment, the above purified extract is hydrolysed in a water-miscible solvent medium, such as methanol, after the pH has been adjusted to from 6 to 8 and preferably to from 7 to 8 (the pH being measured in the methanol), using, for example, an acetic acid-ethyl acetate buffer medium. The ratio of methanol to aqueous medium which is used is about 10/1 by volume and the ratio of purified extract to extraction medium is about 1/20 by weight. Extraction takes place in an oxygen-free atmosphere, such as under nitrogen, after care has been taken to deoxygenate the extraction medium, by for example, de-aerating it at boiling point or bubbling nitrogen through it. The operation is carried out at a temperature of from 20° to 40° C. and preferably at ambient temperature over a period of from 4 to 7 days.

Hydrolysing the tannic acid causes the depsidic bonds between two galloyl groups to be selectively split thereby freeing a mixture of penta-, tetra- and tri-galloyl glucose and methyl gallate and digallate, the pentagalloylglucose forming from 28 to 51% of these compounds, depending on the nature of the raw material and the conditions, more particularly the pH, of hydrolysis.

After the methanol has been evaporated under reduced pressure, the residue is taken up in water in a proportion of residue to water of about 1/5 by weight. Dialysis against pure water is then carried out with membranes of from 1.5 to 2 nm (nanometer) for at least 24 h preferably for 48 h at ambient temperature. This operation enables the small molecules, such as methyl gallate and digallate and the salts used as buffer, to be removed. The aqueous medium may be dried, for example, by lyophilisation or it may be extracted, for example, by an equal volume of ethyl acetate, the solvent is separated from the aqueous medium and is evaporated under reduced pressure and the residue dried, for example, by lyophilisation.

As a variant, the separation of the polygalloyl glucoses may be continued until a fraction is obtained, which contains essentially pentagalloyl glucose, by chromatography on a cellulose column, eluting with, for example, an aqueous solution of acetic acid. The aqueous medium is then extracted by ethyl acetate, the solvent is separated from the aqueous medium and is evaporated under reduced pressure and the residue dried, for example by lyophilisation.

The anti-oxidant extracts may be used for protecting all sorts of foodstuffs or cosmetic products against oxidation.

Foodstuffs into which they may be incorporated, include fats, such as plant oils and animal fats; emulsions, such as mayonnaise, spreads, salad dressings, creams, stock cubes, etc . . . ; moist products containing emulsified fats, such as meat and fish, in the form of emulsions, for example, dried complex foodstuffs, such as vegetables and more particularly, potato flakes, dehydrated soups, cereal-based products, such as structured products, milk foods, whole milk powders, soya powder, etc . . . .

Cosmetic products which are sensitive to oxidation are in the form of aqueous dispersions (lotions, such as shaving foam or after-shave), fluid emulsions (body lotions, make-up removing milks), creams (facial cream, suntan lotion), pastes (masks), etc . . . . Protecting these products against oxidation allows in particular, olefactory problems caused by rancidity to be avoided.

The possibility also exists of incorporating the dried extracts into plastic materials or packaging laminates for foodstuffs or cosmetic products.

Satisfactory results have been obtained by incorporating from 0.01 to 1% and preferably from 0.05 to 0.2% by weight of extract, by any known means, such as in solution or suspension or emulsion, in solvents or liquefied gases, in other words, using a suitable vehicle.

Of course, other anti-oxidant materials, so-called, "secondary" materials, may also be added; these materials, such as ascorbic, tartaric and citric acid or ethylenediaminetetraacetate have a chelating effect on the pro-oxidising materials in the medium. Other secondary anti-oxidant materials, such as sodium ascorbate, metabisulphite or pyrophosphate lower the redox potential of the said medium.

The following examples illustrate the carrying out of the present invention. Percentages and quantities given in the following are by weight unless otherwise specified.

EXAMPLES

EXAMPLE 1

(a) 130 g of diced green carobs are placed in a mixer and extracted by 400 ml of a 96% ethanol solution at ambient temperature for 10 min. The solid residue is recovered by filtration and is re-extracted three times under the same conditions. The ethanolic extracts are combined and evaporated under vacuum at 30° C. 10.4 g of the ethanolic extract of green carob are obtained in the form of a pale brownish-green powder (crude extract).

(b) With a view to effecting a comparison, black tea and cereals (barley, oats, sorghum) are extracted under the following conditions, described with reference to barley. 500 g of commercial barley in the form of 1 mm particles (average value) are crushed and extracted by 1200 ml of a 96% ethanol solution under reflux over a period of 60 min. The solid residue is recovered by filtration and is twice re-extracted under the same conditions. The ethanolic extracts are combined and evaporated under vacuum at 30° C. 3.1 g of crude extract are obtained in the form of a slightly brown powder.

EXAMPLE 2

(a) 500 g of diced fresh green carobs are extracted in a mixer by 1000 ml of methanol for 10 minutes at ambient temperature. The residue is twice re-extracted with 1000 ml of methanol. The methanolic extract is concentrated to 200 ml by evaporation under vacuum at 40° C., 250 ml of water are added and the gallotannins are extracted from the aqueous phase by ethyl acetate. Extraction is repeated 6 times with 500 ml of ethyl acetate each time. The organic phases are combined and the solvent is evaporated under vacuum at 30° C. 21.3 g of purified gallotannins are obtained.

(b) When the same extraction procedure is applied to 80 g of fresh gall nuts, 37 g of purified gallotannins may be recovered.

EXAMPLE 3

100 g of commercial tannic acid(Fluka) are dissolved in 500 ml of 1N phosphate buffer at pH7. The pH of this solution is adjusted to 7 by addition of 400 ml of 1N disodium hydrogenophosphate solution. Purified gallotannins are obtained by extracting 6 times with 250 ml of ethyl acetate. After the phases have been separated, the organic phase is evaporated under vacuum at 30° C. and 80 g of purified gallotannins are obtained.

The 80 g of purified gallotannins are dissolved in 180 ml of 0.5N acetate buffer at pH6. 1600 ml of methanol, which has previously been deoxygenated by heating at boiling point for 1 hour, are added and the pH of the solution is adjusted to 7.5 by addition of 2N acetic acid. The methanolic solution of gallotannins is kept under nitrogen for 7 days at ambient temperature. The solvent is then evaporated under vacuum at 30° C.

Table I below gives the proportions of the hydrolysate constituents (in mol %) which are obtained at different pH values:

TABLE I

| pH of the acetate/MeOH buffer solution | % penta galloyl glucose | % tetra galloyl glucose | % tri-galloyl glucose | % methyl digallate | % methyl gallate |
|---|---|---|---|---|---|
| 7.5 | 51.2 | 19.7 | 3.8 | 4.3 | 21.0 |
| 6.5 | 35.4 | 14.9 | 2.1 | 3.0 | 15.7 |
| 6.0 | 27.9 | 10.9 | 1.3 | 1.8 | 8.2 |

The residue, which mainly consists of penta-O-galloyl-D-glucose and methylgallate, is dissolved in 400 ml of water and the solution is placed in a dialysis bag formed by a membrane which has a pore size of from 1.5 to 2.0 nm (nanometer) to be dialysed against pure water, over a period of 48 h at ambient temperature. Dialysis allows the small molecules (mainly methyl gallate but also traces of methyl digallate and gallic acid) to be removed. The content of the dialysis bag is lyophilised and 38 g of penta-O-galloyl-D-glucose are obtained which is about 90% pure.

The penta-O-galloyl-D-glucose may optionally be purified by passing it over an MN cellulose-300 G column and eluting it by an aqueous solution containing 6% of acetic acid. The penta-O-galloyl-D-glucose which is thus obtained is 97% pure. 3 g of the product may be purified on a column which is 3 cm in diameter and 90 cm in height.

The structure of the polygalloyl glucose was checked by proton nuclear magnetic resonance spectroscopy (NMR) and by high pressure liquid chromatography in comparison with the control products which were obtained by synthetic means, such as pentagalloyl glucose which was produced from tri-O-benzylgalloyl chloride and β-glucose in the presence of pyridine and chloroform to produce β-penta-O-(benzylgalloyl) glucose which was converted by hydrogenation into β-penta-O-galloyl glucose.

EXAMPLE 4

The anti-oxidant activity of the various extracts was determined by comparing them with commercial anti-oxidant extracts by means of the Rancimat accelerated oxidation test, described by J. Frank, J. Geil in "Food Technology 1982, 71", in chicken fat at 100° C. This test gives a very realistic indication of the power to protect the fatty substances against the action of oxygen.

The results in terms of induction time, in hours, are set out in Table II:

TABLE II

| Additive | | Induction time (hours) | | | |
|---|---|---|---|---|---|
| | | Concentration (parts by million) | | | |
| | C.F. | 500 | 1000 | 1500 | 2000 |
| Crude extract according to Example 1a | 3 | 6[1] | 7.3 | 10.5 | n.d. |
| Purified extract according to Example 2a | 3.8 | 8.2 | n.d. | n.d. | n.d. |
| Pentagalloylglucose (90% pure) according to Example 3 | 3.3 | 7.5 | 10.5 | n.d. | 15.3 |
| Commercial tannic acid (Fluka) | 3.8 | 10.2 | n.d. | n.d. | n.d. |
| Alcoholic extract of rosemary (Culinar) | 3.8 | 11.1 | n.d. | n.d. | n.d. |
| Commercial Chinese tannins | 3.8 | 11.5 | 16.8 | n.d. | n.d. |
| Crude extract of sorghum according to Example 1b | 3.5 | 3.2 | 3.5 | n.d. | 3 |
| Crude extract of barley according to Example 1b | 3.5 | 3 | 3.2 | n.d. | 3.4 |
| Crude extract of oats according to Example 1b | 3.5 | 3.5 | 3.6 | n.d. | 3.4 |
| Crude extract of black tea according to Example 1b | 3.5 | 3 | 3 | n.d. | 3 |
| Ellagic acid | 3.5 | 3 | 3 | n.d. | 3 |

Key:
n.d.: not determined
C.F.: chicken fat without additive (control)
[1]not taking into account the fact that only 54% of the dried ethanolic extract is resolubilised in ethanol.

It can be seen that the various extracts of tea and cereals obtained by extraction with ethanol according to Example 1b do not have any anti-oxidant activity (sorghum and tea contain condensed tannins and catechol polymers). Ellagic acid, a derivative of condensed gallic acid, is not anti-oxidant at all.

On the other hand, a comparison of the colour of 1% by weight of rosemary and carob extracts in ethanol shows that the commercial rosemary solution is about 3.7 times more absorbent than the green carob solution according to example 1a in the range of from 650 to 680 nm (nanometer).

The green carob extract according to Example 1a has no smell at 20 cm of a flask containing 5 g; in comparison, even only slight traces of the commercial extract of rosemary have a strong smell.

EXAMPLE 5

The anti-oxidant effect of present extracts in comparison with propyl-, methyl- and octyl gallates on an emulsion of chicken fat in water was examined at 40° C. using the accelerated oxidation test (lipidic peroxidation catalysed by hemin) according to D. Sandmeier, G. Ziegleder in "Fette Seifen Anstrichmittel, 84 11–14 (1982)".

This test is a good means for evaluating the protection by anti-oxidants of emulsion systems and moist products containing them such as the above foodstuffs and cosmetic products against oxidation.

Table III below shows the results in terms of the induction times in minutes:

TABLE III

| Additive | | Induction time (minutes) | |
|---|---|---|---|
| | | Concentration (parts by million) | |
| | C.F. | 200 | 500 |
| Crude extract of carob | 4.5 | n.d. | 6 |
| according to Example 1a | | | |
| Purified extract of carob according to Example 2a | 5.3 | n.d. | 9.3 |
| Purified gall nut according to Example 2b | 5.2 | n.d. | 9.6 |
| Propylgallate | 5.5 | 9 | n.d. |
| Methylgallate | 4.9 | 7.2 | n.d. |
| Octylgallate | 4.9 | 2.2 | n.d. |

Key:
C.F.: Chicken fat without additive (control)
n.d.: not determined

EXAMPLE 6

5 kg of whole wheat are milled into particles of 1 mm average size and are dispersed in 9 liters of deionised water at 20° C. in a vessel provided with a stirrer. The starch is then gelatinised in about 1 minute in an exchanger having a scraped surface which has been heated by steam to 135° C. The suspension is then dried on a cylinder, provided with doctor blades, revolving at 3.5 revolutions/minute at 125° C., the temperature of the product. The film which has formed is scraped off and is formed into flakes of about 1 mm in a granulator. Aluminium cans are filled with 40 g of flakes and sealed.

The degree of oxidation of the flakes is measured by analysing the gases in the head space after it has been left to stand for 1 month at 30° C., according to J. Löliger, "65th Annual Meeting of the Potato Association of America, University of Prince Edward Island, Charlottetown, P.E.I., Canada, 2-6.08.1981". The pentane content gives the degree of oxidation, since on oxidation of linoleic acid this hydrocarbon is formed preferentially. This example of the stabilisation of cereal flour is a good model for complex dried foods, such as those mentioned above.

The following Table IV shows the molar quantity of pentane and the volume percentage of residual oxygen of the gases in the head space.

TABLE IV

| Additive | $10^{-9}$ mol pentane | residual $O_2$ % by volume |
|---|---|---|
| Blank | 2.344 | 19.59 |
| 500 ppm commercial extract of rosemary | 0.077 | 20.80 |
| 1000 ppm commercial tannic acid | 0.478 | 20.42 |
| 1000 ppm carob extract according to Example 1a | 0.106 | 20.61 |
| 1000 ppm pentagalloyl glucose (90%) according to Example 3 | 0.396 | 20.40 |

Key:
Blank: without additive
ppm: part by million

We claim:
1. A method of inhibiting oxidation in foodstuffs subject to oxidation comprising incorporating pentagalloyl glucose in the foodstuff in an amount effective to inhibit oxidation of the foodstuff.
2. A method according to claim 1 wherein the pentagalloyl glucose is penta-O-galloyl-D-glucose.
3. A method according to claim 1 wherein the pentagalloyl glucose is derived from carob.
4. A method according to claim 1 or 2 wherein the effective amount of the pentagalloyl glucose is from

0.01% to 0.2% by weight based on the weight of the foodstuff.

5. A method of inhibiting oxidation in foodstuffs subject to oxidation comprising incorporating purified and hydrolysed non-condensed gallotannins, which are derived from plant material and which comprise polygalloyl glucoses including pentagalloyl glucose, in the foodstuff in an amount effective to inhibit oxidation of the foodstuff.

6. A method according to claim 5 wherein pentagalloyl glucose comprises 28% to 51% of the polygalloyl glucoses.

7. A method according to claim 6 wherein the pentagalloyl glucose is penta-O-galloyl-D-glucose.

8. A method according to claim 5 wherein the polygalloyl glucoses are derived from carob.

9. A method according to claim 5 wherein the effective amount of the polygalloyl glucoses is from 0.01% to 0.2% by weight based on the weight of the foodstuff.

* * * * *